(12) United States Patent
Almogy et al.

(10) Patent No.: US 6,853,446 B1
(45) Date of Patent: Feb. 8, 2005

(54) VARIABLE ANGLE ILLUMINATION WAFER INSPECTION SYSTEM

(75) Inventors: Gilad Almogy, Givataim (IL); Hadar Mazaki, Rehovot (IL); Zvi Howard Phillip, Shoham (IL); Silviu Reinhorn, Mevaseret-Zion (IL); Boris Goldberg, Ashdod (IL); Daniel I. Some, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 189 days.

(21) Appl. No.: 09/641,137

(22) Filed: Aug. 16, 2000

Related U.S. Application Data
(60) Provisional application No. 60/149,215, filed on Aug. 16, 1999.

(51) Int. Cl.[7] .............................................. G01N 21/00
(52) U.S. Cl. .................................................... 356/237.1
(58) Field of Search .......................... 356/237.1, 237.2, 356/237.3, 237.4, 237.5, 237.6; 250/234, 235, 236; 359/201, 202

(56) References Cited

U.S. PATENT DOCUMENTS

| | | | | |
|---|---|---|---|---|
| 4,171,917 A | * | 10/1979 | Pirlet | .......................... 356/608 |
| 4,568,835 A | * | 2/1986 | Imamura et al. | ....... 250/559.41 |
| 4,614,427 A | | 9/1986 | Koizumi et al. | ............. 356/237 |
| 4,632,546 A | * | 12/1986 | Sick et al. | ............... 356/237.5 |
| 4,731,855 A | | 3/1988 | Suda et al. | |
| 4,886,975 A | * | 12/1989 | Murakami et al. | ..... 250/559.41 |
| 4,929,845 A | | 5/1990 | Amir et al. | |
| 5,106,196 A | | 4/1992 | Brierley | ....................... 356/445 |
| 5,125,741 A | * | 6/1992 | Okada et al. | ............. 356/237.2 |
| 5,189,481 A | | 2/1993 | Jann et al. | ..................... 356/73 |
| 5,381,225 A | * | 1/1995 | Kohno | .................... 356/237.5 |
| 5,408,352 A | * | 4/1995 | Peng | ........................... 359/203 |
| 5,486,919 A | | 1/1996 | Tsuji et al. | .................. 356/349 |
| 5,699,477 A | | 12/1997 | McCree | |
| 5,777,746 A | * | 7/1998 | Dlugos | ....................... 356/628 |
| 5,798,829 A | | 8/1998 | Vaez-Iravani | |
| 5,825,482 A | | 10/1998 | Nikoonahad et al. | |
| 5,864,394 A | | 1/1999 | Jordan, III et al. | |
| 5,963,316 A | * | 10/1999 | Miura et al. | ............. 356/237.3 |
| 5,982,921 A | | 11/1999 | Alumot et al. | |
| 6,219,168 B1 | * | 4/2001 | Wang | ......................... 359/216 |

FOREIGN PATENT DOCUMENTS

| | | |
|---|---|---|
| EP | 1582868 A1 | 2/1994 |
| WO | WO99/14575 | 3/1999 |

OTHER PUBLICATIONS

PCT Notification of Transmittal of the International Search Report or the Declaration dated Dec. 12, 200.

* cited by examiner

*Primary Examiner*—Hoa Q. Pham
(74) *Attorney, Agent, or Firm*—McDermott, Will & Emery (57) ABSTRACT

A variable illumination angle inspection system is provided, including a light source providing a light beam and a scanner imparting scanning deflection to the light beam to provide a scanning beam approaching a substrate at a first angle. A deflection element is selectively insertable into an optical path of the scanning beam to deflect the scanning beam so as to cause the scanning beam to approach the substrate at a second angle.

24 Claims, 7 Drawing Sheets

VARIABLE ANGLE ILLUMINATION WAFER INSPECTION SYSTEM

RELATED APPLICATIONS

This application claims priority from U.S. Provisional Patent Application No. 60/149,215, filed Aug. 16, 1999, and is incorporated herein by reference.

BACKGROUND OF THE INVENTION

Wafer inspection systems are well known in the art. One conventional system, embodied in U.S. Pat. No. 5,699,447 uses normal illumination and bright-field detection (i.e., the illumination approaches the wafer at ninety degrees thereto). Another type of conventional system, as embodied in U.S. Pat. No. 5,825,482 uses oblique illumination and dark-field detection (i.e., the illumination approaches the wafer obliquely). A third type of system, as embodied in U.S. Pat. No. 5,982,921, uses normal illumination and dark field detection. All of these conventional approaches have advantages and disadvantages, some of which relate to the particular application or situation in which the system is used.

Under normal illumination, the surface of the object viewed is normal to the optic axis of the objective lens and light is used to illuminate the object. In a bright field system, light reflected back to the objective lens in a direction substantially parallel to the incident beam is used to form an image. Hence, surfaces that are reflective and perpendicular to the light rays appear bright and features that are nonreflective or oblique reflect less light back to the objective lens and appear darker. A dark field system may be implemented with either normal or oblique illumination. In either case, light that is scattered away from the optical axis is collected by dark field detectors positioned at an angle to the surface being viewed to form an image. Inclined surfaces of features such as ridges, pits, scratches, and particles therefore appear bright, providing enhanced contrast of these features from subtle topographic features. Thus, reflective features that normally appear bright in bright field illumination are completely black in darkfield illumination and subtle features that are undetectable using bright field illumination may be readily observed with dark field illumination.

In a laser-scan wafer inspection scenario it is sometimes preferable to illuminate the wafer at an angle normal to the wafer surface, while at other times preferable to use oblique illumination, depending on the details of the wafer materials, patterns and defects. The optical scattering characteristics of semiconductor wafers vary dramatically as the wafers proceed from one step to the next of the IC production flow. Some layers (such as bare silicon) are very smooth whereas some others (such as deposited aluminum) can be very rough and grainy.

It is well known that oblique illumination angles help reduce the unwanted optical scattering of the grains and roughness by the "Lloyd's mirror" effect (a destructive interference of the incident and reflected light at the surface which substantially reduced scatter from roughness and grains whose height from the surface is much less than the wavelength of the incident light, especially for metallic surfaces). Oblique illumination angles have, however, some limitations which make them less useful than normal illumination for some layers. One deficiency of oblique illumination angles is the inability of the light to penetrate between dense lines, such as those used in poly-silicon or metal interconnects. Another deficiency of oblique illumination is the dependence of the scattered signal on the direction of the substrate features (i.e., the loss of the symmetry which exists with normal illumination).

In practical inspection systems it is often desired to have replaceable optical elements which allow determination of the spot size. Such a system can thus be optimized for scanning with a large spot and obtaining a very high scan speed although a limited sensitivity; or, on the other hand, for scanning with a small spot and obtaining a very high sensitivity but at a lower scan speed. For normal illumination this is quite straightforward to do and only the classical resolution limits how small the spot can become. For oblique illumination, however, very small spots cannot be obtained due to the additional geometrical factor which introduces spot spread across the substrate plane which is inclined to it.

Accordingly, a need exists in the art for an improved wafer inspection system selectively and advantageously permitting use of either normal scanning illumination or oblique scanning illumination, based on the particular optical scattering characteristics of a semiconductor wafer at a time of inspection.

SUMMARY OF THE INVENTION

An advantage of the present invention is a wafer inspection system selectively and advantageously permitting use of normal scanning illumination or oblique scanning illumination to optimize the inspection characteristics of a scanned layer.

According to the present invention, the foregoing and other advantages are achieved in part by a variable illumination angle substrate inspection system. The variable illumination angle substrate inspection system comprises: a light source providing a light beam; a scanner imparting scanning deflection to the light beam to provide scanning beam approaching the substrate at a first angle; and a deflection element selectively insertable into optical path of the scanning beam and deflecting the scanning beam so as to approach the substrate at a second angle.

Another aspect of the present invention is a variable illumination angle inspection system for inspecting a substrate including a light source providing a light beam and a scanning element adapted to output the light beam along a first optical path to the substrate, the first optical path including a portion incident to the substrate and forming a first angle relative to the substrate. A deflection element is selectively introduced into the first optical path to output the light beam along a second optical path to the substrate, the second optical path including a portion incident to the substrate and forming a second angle relative to the substrate, wherein the first angle is different from the second angle.

In still another aspect, the present invention provides a deflection element for use in a variable illumination angle substrate inspection system. This deflection element includes a first deflecting surface and a second deflecting surface, wherein each of the first and second deflecting surfaces include a mirrored surface. The first deflecting surface is disposed at an angle with respect to said second deflecting surface so that an illumination beam entering the deflection element from a first direction is output from the deflection element in a second direction.

For the above reasons, and for reasons discussed herein, the present invention can therefore be optimized for the particular characteristics of a scanned layer.

Additional features and advantages of the present invention will become readily apparent to those skilled in the art from the following detailed description, wherein only preferred embodiments of the invention are shown and described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF THE INVENTION

Figure 1:
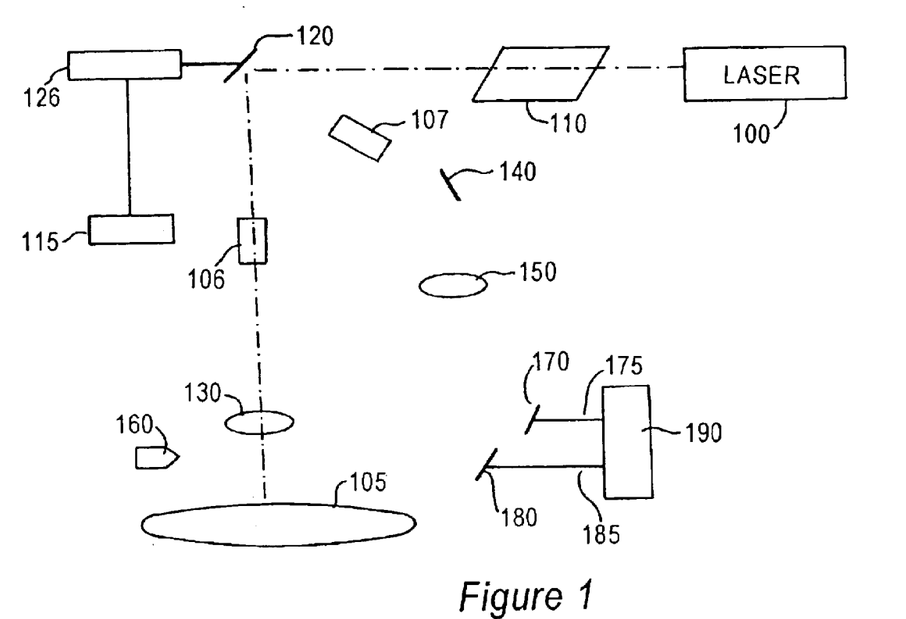
FIG. 1 depicts an embodiment of a system according to the present invention, wherein the illumination is set to be normal.

FIG. 1 illustrates a first embodiment of the invention. Laser 100, such as an argon laser or other suitable high intensity laser beam source, provides a light beam which is used to scan the surface of a semiconductor wafer or substrate 105 held by a vacuum chuck. Conventional optics 110 are used to shape the light beam and may include, for example, a beam expander and cylindrical lenses (not shown). The foregoing components and their principles of operation are well-known and are therefore not described herein in detail.

A mechanism for scanning the laser beam is provided. This mechanism for scanning the laser beam may include, as well known in the art, a galvanometric scanning planar mirror, a rotating polygon mirror, an acousto-optic deflector (AOD), or any other mechanism for imparting the requisite laser scan motion to the laser beam, wherein this mechanism is represented in FIG. 1 by reference numeral 120 and is hereinafter referred to equally as scanning element 120. Additionally, a mechanism for deflecting the scanned beam toward a preferred optical channel (e.g., a normal or an oblique illumination channel) is provided. The mechanism for deflecting may include, for example, a movable mirror which can be rotated to direct the beam toward either of the channels, a mirror on a linear actuator to move it in and out of the optical path, or an AOD. Although various configurations and combinations of the mechanism for scanning and the mechanism for deflecting are discussed in additional detail below, the examples provided and illustrated are not intended to be limited and numerous other combinations and subcombinations of the mechanism for scanning and the mechanism for deflecting may be provided in accord with the invention.

In one basic configuration, the scanning element 120 includes a galvanometric scanning planar mirror rotated by a motor 126 able to adjust an angle of the mirror by fine predetermined increments in response to scanning instruction signals from a scanning controller 115, as known to those skilled in the art. In such an embodiment, the mechanism for scanning and the mechanism for deflecting are advantageously incorporated into a single element. The scan takes place around a plurality of central positions wherein each central position corresponds to a deflection of the scanned beam in preferred directions, such as along normal and oblique illumination channels. Two such illumination channels are shown in FIGS. 1 and 2, which respectively illustrate one central position corresponding to a normal illumination path or channel and another central position corresponding to an oblique illumination channel.

Scanning element 120 deflects the light beam in a predetermined direction, such as toward the semiconductor wafer or substrate 105 or toward an optical device such as an objective lens 130 or mirror 140. The scanning can be performed, for example, along a first axis, such as the X-axis, while the wafer is moved by a scanning stage (not shown) along a second axis perpendicular to the first axis, such as the Y-axis. Other combinations of process variables such as the scanning speed, length of the scanning line, distance between adjacent lines, and light beam spot size can be employed to practice the present invention, as desired by the user.

In the position depicted in FIG. 1, the tilt angle of scanning element 120, comprising a galvanometric scanning planar mirror, is set so that the beam is directed toward wafer 105 at a normal angle (e.g., along a Z-axis normal to the X-axis and Y-axis). In a manner known to those skilled in the art and not described in detail herein, optical relay 106 typically comprises a pair of lenses used to relay light between the scanning element 120 and objective 130, which focuses the scanned beam onto the wafer. Dark field detector 160 preferably includes four photomultiplier tubes (PMTs), such as manufactured by Hamamatsu of Japan, or photo-diode detectors spaced 90° from one another and arranged at an angle of about 45° with respect to the X and Y axes of the wafer 105 to detect light scattered off features inclined with respect to the X and Y axes of the wafer in a manner known to those skilled in the art. A greater or lesser number of PMTs or photodiodes may be used and the arrangement of these detectors may also be varied to optimize dark field detection in accord with particular applications. As shown in FIG. 1, mirror 140, objective 150, first mirror 170, second mirror 180, and actuator 190 are disengaged from the optical path of the scanning light beam.

Figure 2:
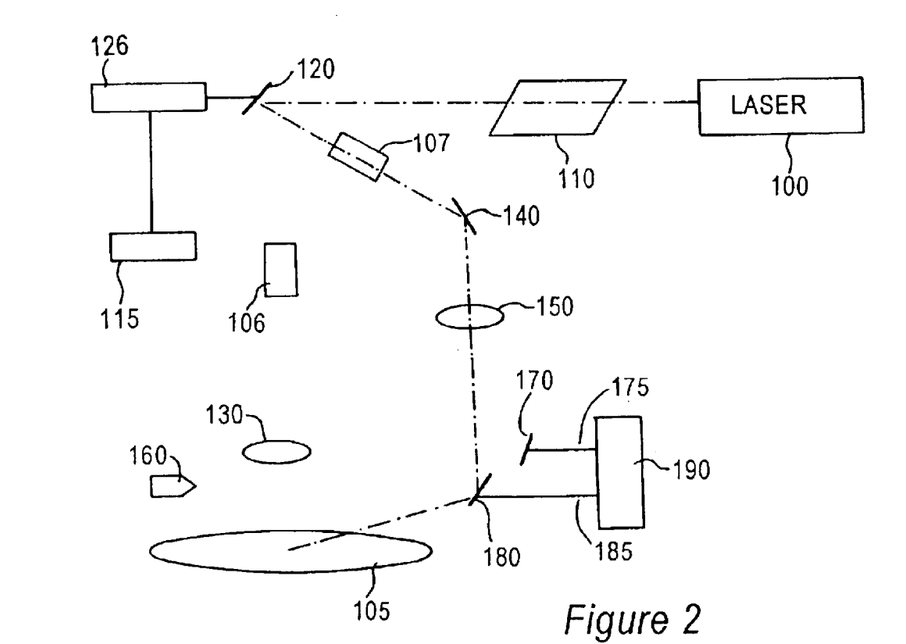
FIG. 2 depicts the system of FIG. 1, wherein the illumination is set to be oblique at a first angle.

FIG. 2 depicts the system of FIG. 1 in an oblique illumination mode. In this mode, the tilt of the scanning element 120 planar mirror is changed to deflect the scanned beam through optical relay 107 and toward mirror 140. Mirror 140 deflects the light toward and through objective 150. Actuator 190 introduces one of a plurality of mirrors 170, 180 into the path of the beam. Although only two mirrors are depicted in FIG. 2, the invention may advantageously include more than two mirrors. Each mirror 170, 180 is connected to a respective translatable actuator arm 175, 185. Mirror 180 receives incident light from scanning mirror 120 and any intervening optical elements and deflects the light beam toward wafer 105 at an oblique angle to provide oblique illumination.

Figure 3:
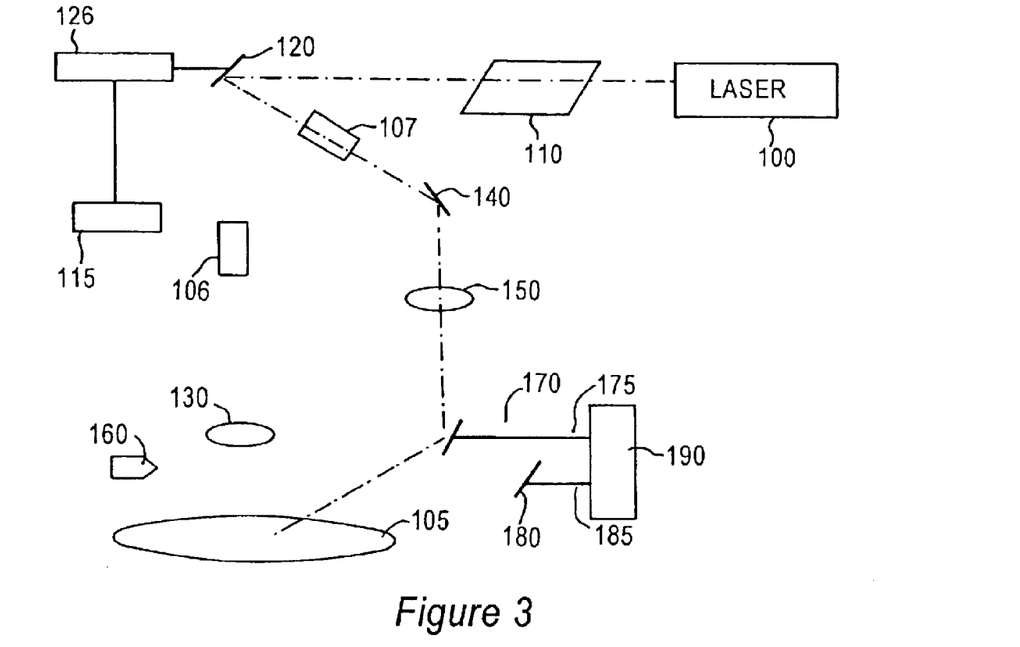
FIG. 3 depicts the system of FIG. 1, wherein the illumination is set to be oblique at a second angle.

To change the angle of illumination, actuator 190 introduces another mirror, mirror 170, to intercept the light beam output from the scanning mirror 120 and retracts the de-selected mirror 180, as shown in FIGS. 2 and 3. Insertion of mirror 170 having a different degree of tilt or angle than the de-selected mirror (i.e., mirror 180) provides a change in the angle of illumination, as shown in FIG. 3. A plurality of mirrors aligned at predetermined angles are used to direct incident light from each of the pre-aligned mirrors to the same location on wafer 105 from slightly different angles. Alternatively, a single mirror can be used in lieu of mirrors 170, 180, wherein the mirror is selectively tilted at a desired angle about selected axes relative to an incident light beam to obtain a required illumination angle and thereby alter the location of the illumination spot incident on the wafer 105.

Figure 4:
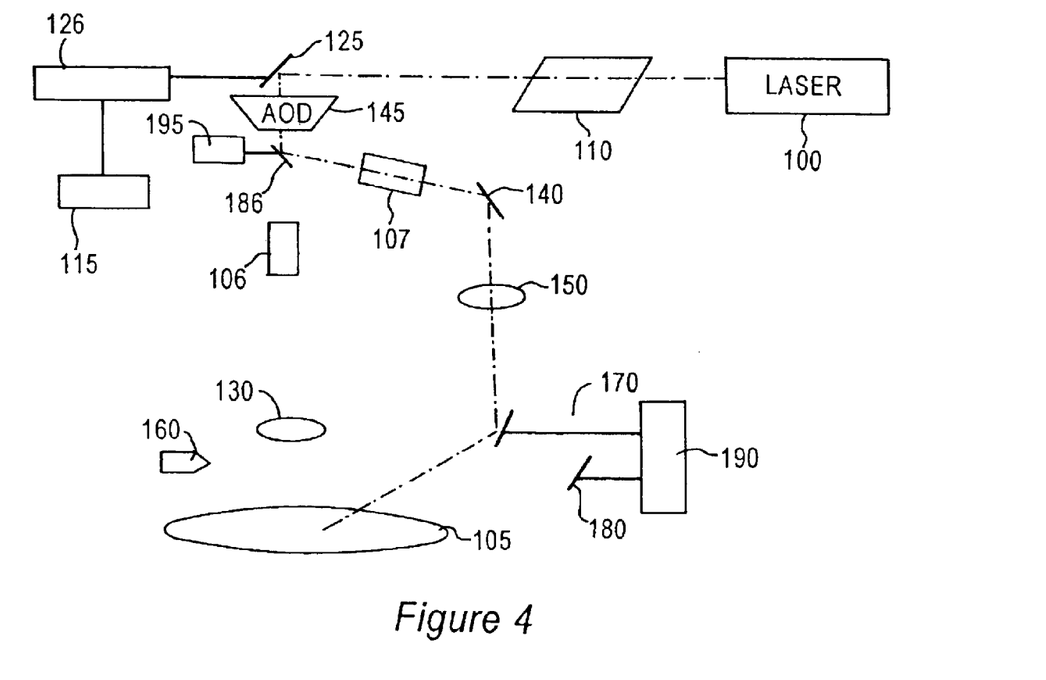
FIG. 4 depicts a second embodiment of the system according to the present invention, wherein tilt is provided after the scanning element.

FIG. 4 depicts another variation of the present invention wherein scanning element comprises acousto-optic deflector (AOD) 145, such as that manufactured by Crystal Technologies Inc. (CI) of the United States and mirror 125. As known to those skilled in the art, AOD scanning element 145 includes, for example, a transducer portion for generating sound waves to modulate the optical refractive index of a selected acoustooptic crystal and deflect the light beam and cause an incident light beam to change direction to and trace a path across wafer 105. Mirror 125 directs the light beam output from optics 110 into AOD scanning element 145. Alternatively, laser 100 and optics 110 can be positioned to directly input the light beam into the AOD scanning element or rotating mirror 145. Oblique illumination is provided by actuator 195, which introduces deflection mirror 186 into the scanning beam to deflect the scanning beam toward mirror 140, whereupon the scanning beam follows a path similar to that illustrated in FIGS. 1–3. To provide normal illumination, actuator 195 withdraws deflection mirror 186 from the optical path of the light beam output by the AOD scanning element 145.

Figure 5:
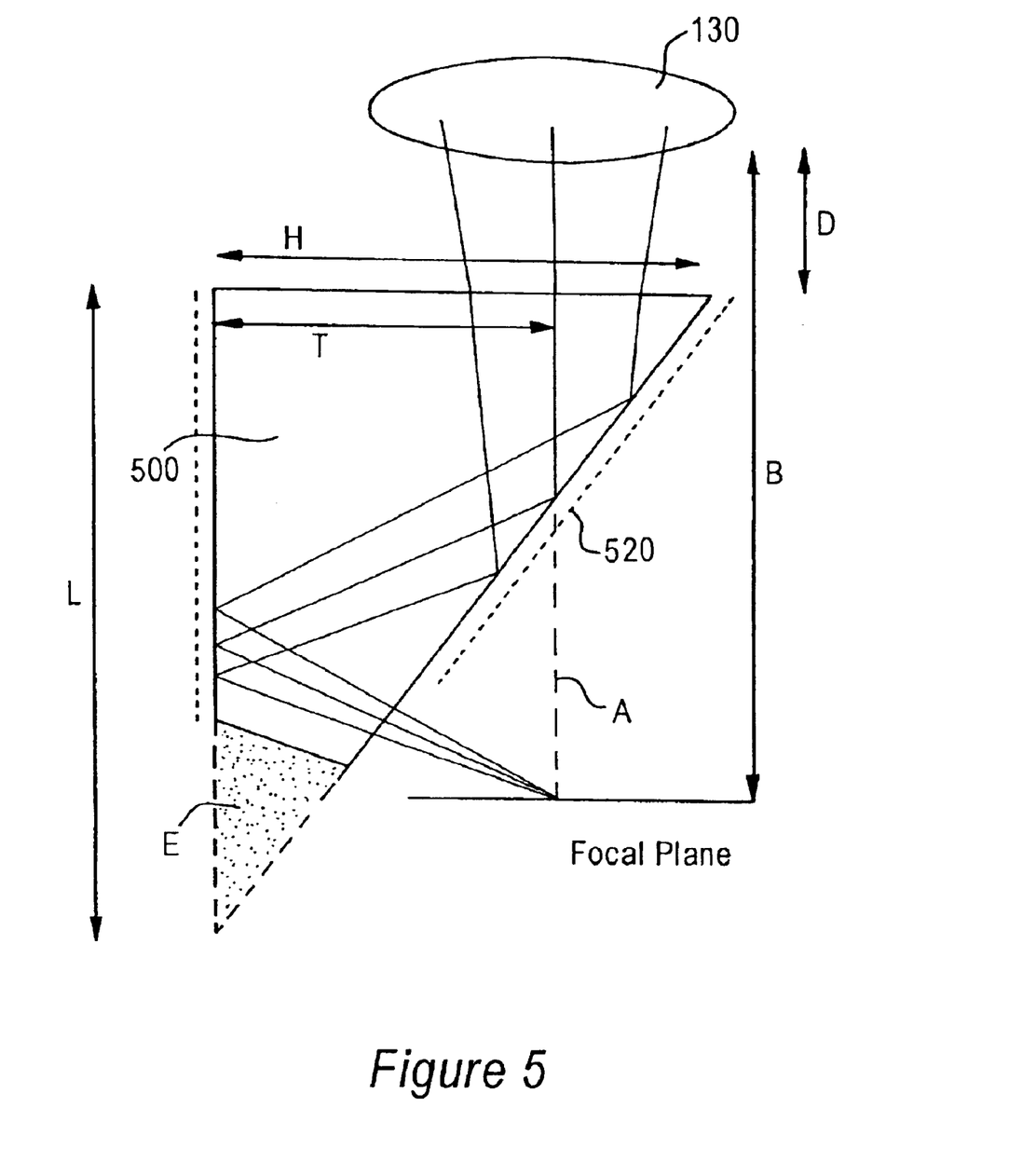
FIG. 5 depicts an oblique illumination adapter useable in accord with the invention.
Figure 6:
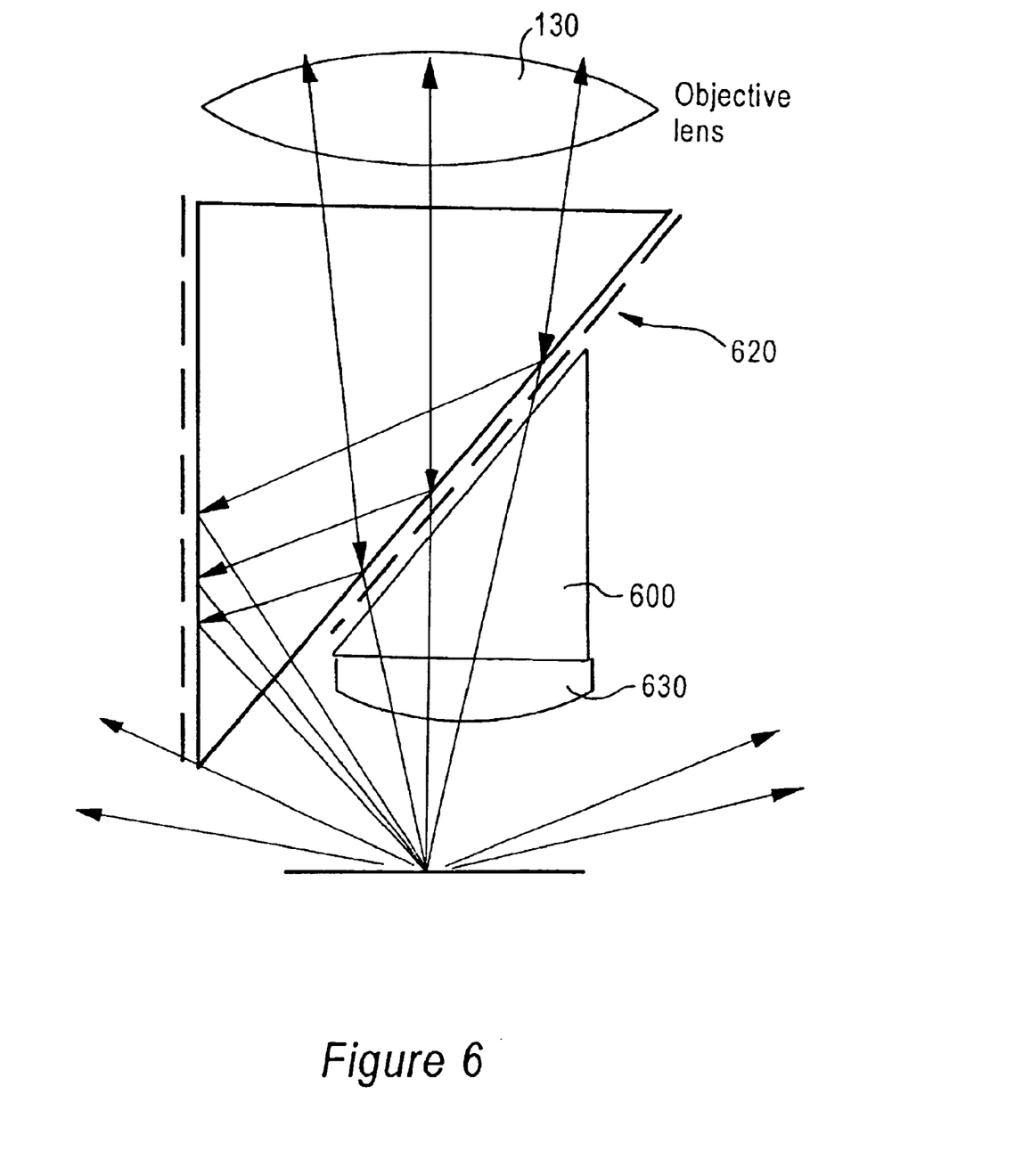
FIG. 6 depicts the oblique illumination adapter of FIG. 5 used in conjunction with an autofocus device.
Figure 7:
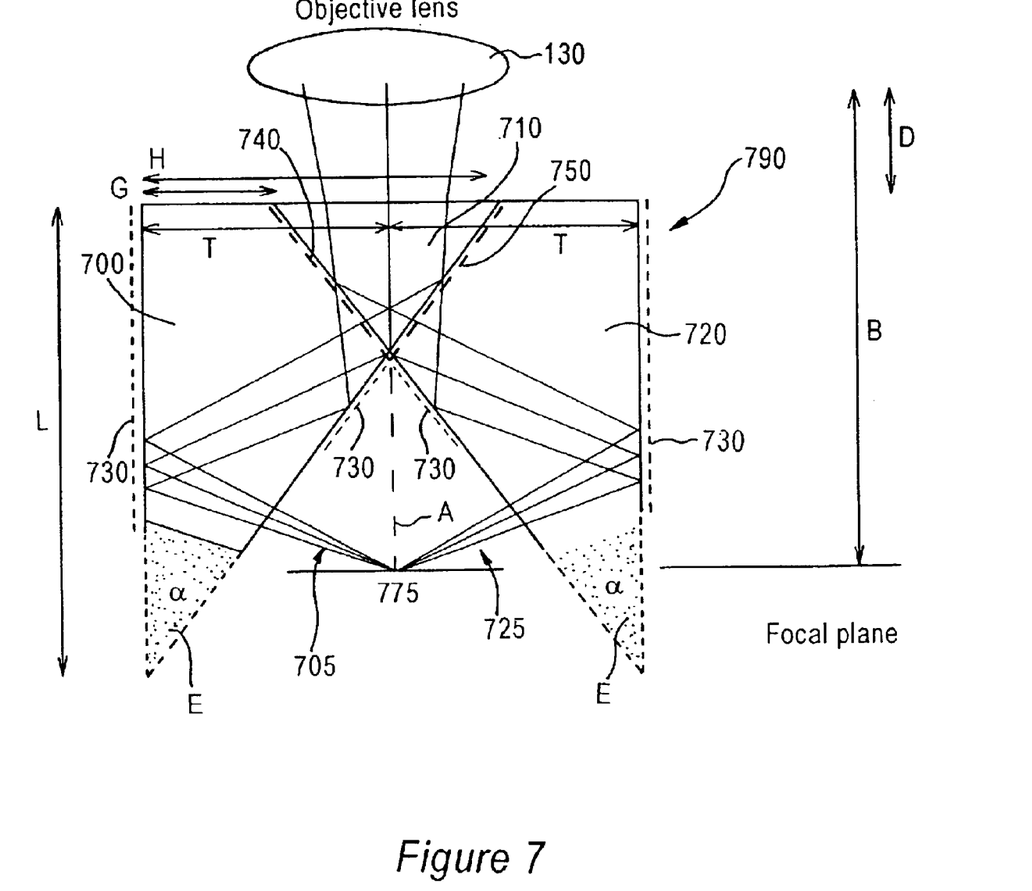
FIG. 7 depicts another type of oblique illumination adapter useable in accord with the invention.

The embodiments illustrated in FIGS. 1–4 provide an actuator to selectively insert deflection mirrors into the optical path to obtain a desired angle of illumination. Likewise, in accord with the above discussion and the embodiment depicted in FIGS. 5–7, one or more actuators may selectively insert different objectives into the optical path and may selectively insert glass wedges into the optical path, individually or in combination with an objective. As shown in FIGS. 5–7, these glass wedges are inserted under objective 130 (shown in FIGS. 1–4), to deflect an illumination beam normal to the substrate to a direction oblique to the substrate. As will be appreciated by those skilled in the art, the objective depicted above the respective deflection elements in each of FIGS. 5–7, described below, do not necessarily correspond to objective 130, as depicted, and may be positioned elsewhere in the scanning system for a similar purpose.

Thus, in accord with the above, oblique illumination may be obtained from a normal illumination scanning beam by introducing a different optical deflecting device, such as a prism or mirrored glass wedge, into a normal illumination scanning beam. This may be accomplished, for example, using actuator 195 and translatable actuator arm 185, or may be accomplished in any other manner of introducing an optical element into an optical path as can be appreciated by those skilled in the art.

For example, the optical deflecting element may include a partially mirrored glass wedge 500 disposed under objective lens 130, as shown in FIG. 5. Proper choice of the wedge geometry and glass index of refraction allows focusing of the oblique illumination at the same distance and position as illumination light provided in the normal direction along axis A coincident with a center of objective lens 130. In other words, FIG. 5 depicts a preferred configuration wherein the oblique-illumination focal point coincides with the normal-illumination focal point. In this aspect of the invention, the glass wedge is made of SFL6 glass, however, other variants of the glass wedge could utilize other conventional glasses, such as BK7. The glass wedge apex angle α is 30°, the width H at the upper surface is 10.88 mm, and the length L at the leftmost surface is 18.8 mm. End portion E may optionally be removed, as indicated in FIG. 5, by the shading of end portions E to facilitate positioning of the glass wedge 500 relative to the substrate. It is to be understood that FIG. 5 is a representation of an optical deflecting element in accord with the invention and should not be construed to define or illustrate precise dimensions.

The original back focal length B is 15.8 mm and the objective back focal plane of objective lens 130 is positioned a distance D, 4 mm, from the top of the glass wedge. The distance T from the leftmost surface of the glass wedge to the chief ray, the ray passing through the center of the aperture stop of the optical system, from the objective is 8.08 mm. In the above configuration, the numerical aperture (NA) of the lens is selected to be 0.125. A range of NA between about 0.04 and 0.125 may be used, however, based on the selected parameters.

Although this aspect utilizes a right angle triangular prism, other shapes such as irregular polygonal shapes may also be utilized in accord with the invention. Additionally, the above defined dimensions embody only one specific example of a glass wedge providing oblique illumination and many other combinations of materials, angles, and dimensions may be employed to achieve the above described result in accord with the invention. In other words, in the example above, an apex angle of 30° is chosen to produce an angle of incidence of 60°, however, other incidence angles may be obtained by using different wedge 500 geometries and properties using the above principals and it is to be understood that the illustrative parameters above relate to a specific example and are in no way limiting to the inventive concepts disclosed herein. Further, although the glass wedge 500 is described as being positionable under objective lens 130, other variants may be advantageously be employed. For example, glass wedge 500 may be incorporated with objective lens 130 or may be embodied within a common structure so as to be simultaneously positionable within incident illumination light.

As shown in FIG. 5, light output from objective lens 130 is reflected off of mirrored surfaces 520 such as, but not limited to, reflective aluminum or aluminum alloy coatings, and focused obliquely on the normal-illumination focal point. Light scattered back through the prism and objective to the bright field detector may be used and collected for inspection purposes. Moreover, all light diffused by the wafer or specimen in any direction can be collected and used for processing.

In an automated inspection system, an autofocus mechanism is desirable. Some autofocus systems applicable to normal illumination configurations utilize the light reflected back through the objective. Such an autofocus mechanism may be accommodated by a modified unidirectional oblique illumination adapter. In the modified adapter, an autofocus prism 600 such as that depicted in FIG. 6 may be applied to the glass wedge 500 depicted in FIG. 5 to permit auto-focus by a secondary optical path. As with the embodiment illustrated in FIG. 5, one or more actuators may selectively insert different objectives into the optical path and may selectively insert glass wedge 500 into the optical path, individually or in combination with an objective and/or autofocus prism 600.

In this embodiment, the mirrored surface 520 on glass wedge 500 is replaced with a mirrored coating 620 transmitting a portion of the incident light. A bright specular reflection in the normal direction can then be at least partially transmitted back through the mirrored coating 620 to the objective lens 130 to permit bright field detector and autofocus operation. With reference to FIG. 5, a portion of the incident light from objective lens 130 is transmitted through mirrored coating 620, whereas a remaining portion of the light follows the illustrated oblique illumination path. For example, the light transmitted though mirrored coating 620 could comprise about 5–10% of the light, whereas the remaining portion of the light following the oblique illumination path would correspondingly comprise 90–95% of the light. Autofocus prism 600 may be configured to match the focal height of the normal illumination with the oblique illumination alone or in combination with a low power cylindrical lens 630, as illustrated in FIG. 5. However, the system is not limited to autofocus based on illumination path optics and is aptly suited for autofocus based on other principles, such as PSD in reflected light path for example, as well. For example, autofocus may be implemented when the primary illumination beam is oblique and the detector is positioned to detect and utilize light the incident light reflected from the wafer, in a manner known to those skilled in the art. Moreover, the system of the invention can work with or without autofocus.

Further, oblique illumination may be provided bidirectionally by replacing the glass wedge of FIG. 5 with a three-section adapter 790 comprising glass wedges 700, 710, and 720, as shown in FIG. 7. Surfaces 730 are covered with a 100% reflection mirrored coating, such as an aluminum or aluminum alloy layer. Surface coating 740 is a polarizing beamsplitter coating provided at the interface of sections 700 and 710 to transmit specified portions of s-polarized light and p-polarized light (hereinafter represented by $s_{740}\%$ and $p_{740}\%$ respectively to reflect the transmitted percentages of incident light component) and reflect remaining light components that are not transmitted. In this embodiment, the polarization of the incident light is controlled to include both s- and p-polarizations, such as through the use of a quarter-wave plate or a half-wave plate. Surface coating 740 is provided to transmit a greater percentage of s-polarized light than p-polarized light (i.e., $s_{740}\% > p_{740}\%$). Surface coating 750 is a polarizing beamsplitter coating provided at the interface of sections 710 and 720 to transmit approximately $s_{750}\%$ s-polarization and $p_{750}\%$ p-polarization and reflect remaining light components that are not transmitted, wherein $p_{750}\% > s_{750}\%$. Therefore, oblique beam 705 emerging from section 700 will be primarily s-polarized, while the oblique beam 725 emerging from section 720 will be primarily p-polarized. By way of example, one advantageous configuration employs a surface coating 740 wherein $s_{740}=99\%$ and $p_{740}=1\%$ and a surface coating 750 wherein $s_{750}=1\%$ and $p_{750}=99\%$. Naturally, surface coatings may be used to transmit any desired component or components of light and are not limited to the above example.

Additionally, the surface coatings 740 and 750 may comprise a plurality of layers adjacent one another, wherein the function of the coatings 740 and 750 are shared by the plurality of layers. For example, the s-polarizing beamsplitter coating 740 may utilize more than one layer, wherein the combination of layers produces a desired polarization level. Thus, a first s-polarizing beamsplitter coating 740 having a first polarization ratio may be used in conjunction with a second s-polarizing non-beamsplitter coating 741 (not shown) having a second polarization ratio provided just after the first s-polarizing beam splitter coating 740 to produce, in combination, the desired polarization level.

Alternately, the surface coatings 740 and 750 may be replaced by combinations of half-wave plates and polarizing beamsplitter coatings. For example, instead of s-polarizing beamsplitter coating 740, a p-polarizing beamsplitter may be disposed between two half-wave plates. The first half-wave plate would rotate the incoming polarization by 90 degrees, turning the s- into p- and vice versa, as known to those skilled in the art. The p-polarizing beamsplitter coating would transmit p- (originally s-) and the second half-wave plate would rotate the incoming polarization another 90 degrees, turning the incoming p-polarization into an output s-polarization. This embodiment additionally contemplates other combinations of wave plates, such as quarter waveplates, and/or polarizing beamsplitter coatings to achieve a desired output polarization ratio. One polarization ratio suitable for use with the system of the invention is approximately 99:1.

The three-section adapter 790 is introduced into the light path, such as by actuator 190 and translatable actuator arm 185, to deflect light incident thereon toward a wafer or substrate at an oblique angle and focus the oblique illumination at the same distance and position as illumination light provided in the normal direction along axis A coincident with a center of the objective lens 130. In this aspect of the invention, the glass wedge is made of SFL6 glass, however, other variants of the three-section adapter 790 could utilize other conventional glasses, such as BK7. The glass wedge apex angle $\alpha$ is 30°, the width H at the upper surface is 10.88 mm, and the length L at the leftmost surface is 18.8 mm. End portion E may optionally be removed, as indicated in FIG. 7, by the shading of end portions E to facilitate positioning of the glass wedge relative to the substrate.

The original back focal length B is 15.8 mm and the objective back focal plane of objective lens 130 is positioned a distance D, 4 mm, from the top of the three-section adapter 790. The distance T from the leftmost or rightmost surface of glass wedges 700 and 720, respectively, to the chief ray, the ray passing through the center of the aperture stop of the optical system, from objective 130 is 8.08 mm. The numerical aperture (NA) of the lens is 0.125. A range of NA between about 0.04 and 0.125 may be used, however, based on the selected parameters. It is to be understood that FIG. 7 is a representation of an adapter 790 deflecting a light beam in accord with the invention and should not be construed to define or illustrate precise dimensions.

The above defined dimensions embody only one specific example of glass wedges 700, 710, and 720, cooperatively used to provide oblique illumination and it is to be understood that many other combinations of materials, angles, and dimensions may be employed to achieve the above described result in accord with the invention and the illustrative parameters above relate to only one specific example and are in no way limiting to the inventive concepts disclosed herein. Additionally, three-section adapter 790 permit continued used of autofocus systems, as described above and as known to those skilled in the art, even when the primary illumination beam is oblique. Still further, as with the previous embodiments, one or more actuators may selectively insert different objectives into the optical path and may selectively insert three-section adapter 790 into the optical path, individually or in combination with an objective and/or focusing device.

In the configuration illustrated in FIG. 7, light output from objective lens 130 is reflected from mirrored surfaces 730 and is focused obliquely on the normal-illumination focal point. The specular reflections from each beam 705, 725 will retrace the path of the oppositely polarized beam. For example, oblique beam 705 is specularly reflected off surface 775, or a particle or topographical feature thereon or therein. This reflected beam 705 is in turn reflected off of reflective surface 730 on the rightmost side of wedge 720 directly toward surface coating 750 or indirectly toward surface coating 750 by way of opposing reflective surface coating 730. As previously noted, surface coating 750 transmits about 1% of the s-polarized portion of the beam 705 and about 99% of the p-polarizated component and such portion of reflected beam 705 is transmitted through the p-polarizing beamsplitter coating 750. Similarly, a portion of reflected beam 725 is transmitted through the s-polarizing beamsplitter coating 740. These transmitted portions continue back through the objective to a bright field detector and autofocus. In addition to other autofocus mechanisms, this device permits autofocus to be accomplished by verifying that the image consists of a single, rather than double, scan line.

Figure 8A:
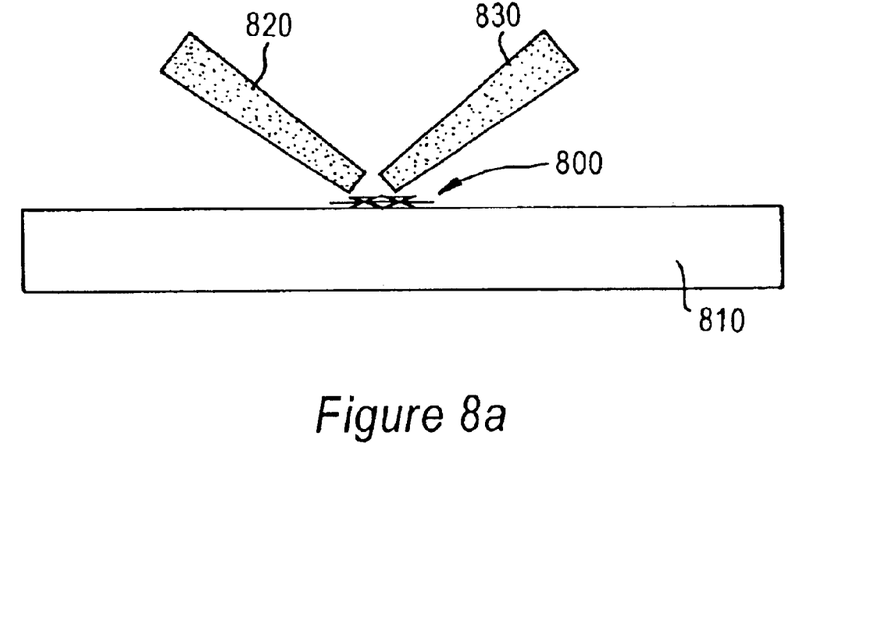
FIGS. 8a–8b illustrate use of bidirectional illumination in defect detection.
Figure 8B:
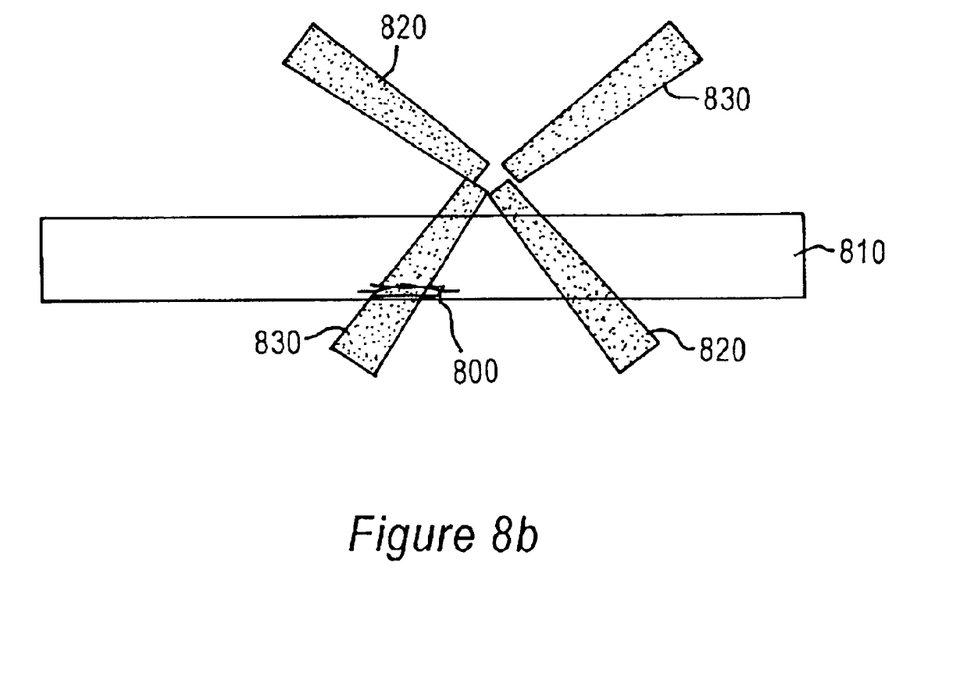

Further, because the two polarizations propagate in opposite directions, the scattered light has an azimuthal polarization dependence which can assist in defect discrimination. For example, the bidirectional illumination utilizing s- and p-polarized light, as described above, affords a small degree of height discrimination of defects, as shown in FIGS. 8a and 8b, on and within a transparent substrate 810. Images of a small feature 800 on the surface of the substrate 810 appear to in one place in images taken from different darkfield perspectives since the incident beams overlap, as shown in FIG. 8a. However, the image is doubled if feature 800 is below the surface of the substrate, as shown in FIG. 8b, or above the surface of the substrate since the incident beams 820, 830 are separated and the feature 800 is illuminated twice during a scan. Although the effect illustrated in FIGS. 8a and 8b is generally not pronounced since the effect requires the vertical distance from the feature to the surface of the substrate to be comparable to or larger than the spot size, the above described effect provides useful information. Further, noisy underlayers will be smoothed as the signal will consist of two superimposed noisy images which incoherently add to reduce the noise. Also, since the polarization of the bidirectional beams 820, 830 is orthogonal, the beams will not produce a pronounced interference pattern.

Figure 9:
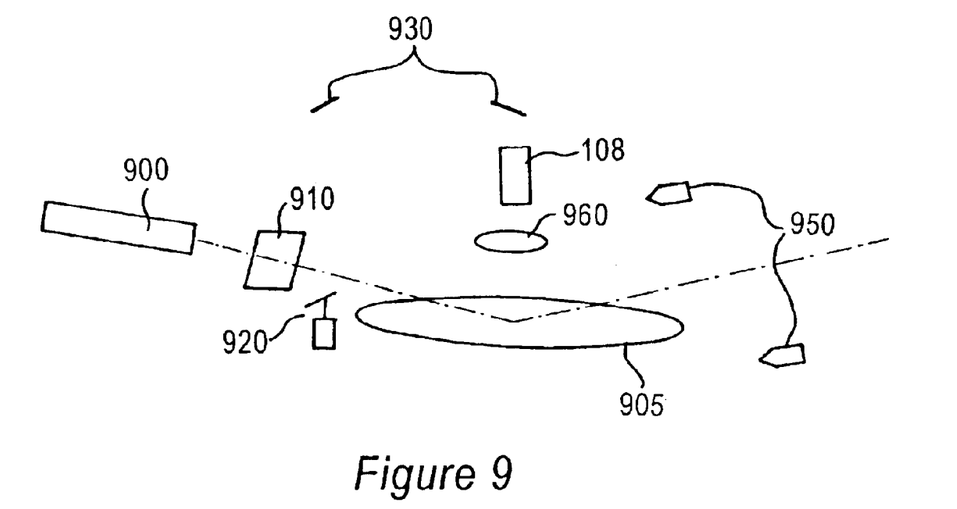
FIG. 9 depicts an embodiment of the invention wherein illumination is set to be oblique.
Figure 10:
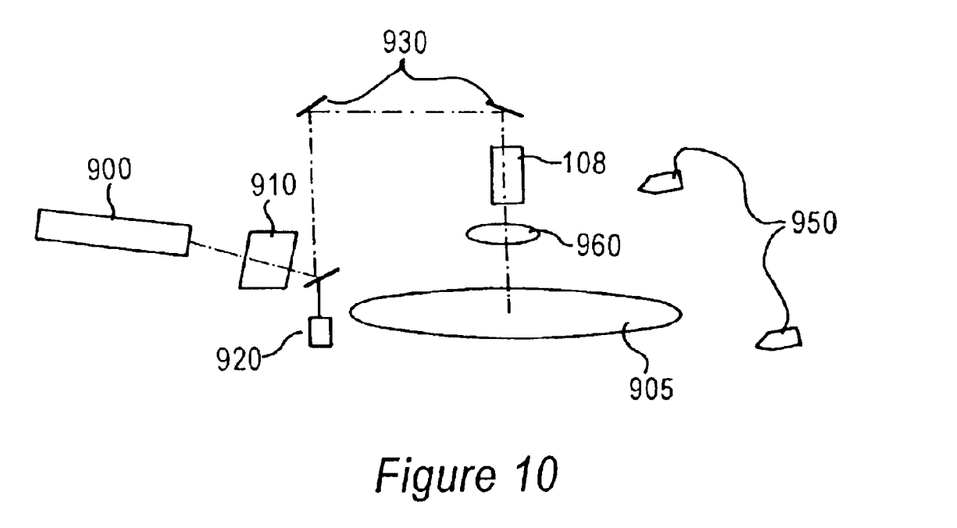
FIG. 10 depicts the embodiment of FIG. 9, wherein illumination is set to be normal.

Another embodiment of the present invention is shown in FIG. 9, wherein the laser illumination is provided obliquely, but may be redirected to provide normal illumination. Specifically, laser 900 outputs a light beam into optics 910, which shapes the beam and provides scanning deflection employing, for example, an AOD scanning element or mirror (not shown). Optics 910 may include, for example, a beam expander and cylindrical lenses (not shown) or other optical shaping elements known to those skilled in the art. Additionally, optical relay may be provided to relay light from laser 900 to objective 960 and dark field detectors 950 may be used to collect scattered light from the wafer 905 to permit detection of particles and defects, as commonly known by those skilled in the art. When normal illumination is needed, actuator 920 introduces a deflection mirror to deflect the light towards mirrors 930, through optical relay 108, and through objective 960 to a selected substrate coordinate, the first optical path including a portion incident to the substrate 905, as shown in FIG. 10.

As will be appreciated by those skilled in the art, the above systems provide a scanning beam arranged to scan an entire wafer in either a normal or an oblique mode. Moreover, with the assistance of scanning controller 115, the system may be adapted to provide selective normal or oblique scanning of individual portions of the wafer to, for example, enhance defect detection of those areas. In particular, the invention set forth in the appended claims permits detailed examination of specific coordinates of interest, as well as global examination of entire wafers from a preferred perspective.

Thus, the invention provides an apparatus for selectively and advantageously permitting use of normal scanning illumination or oblique scanning illumination to optimize the inspection characteristics of a scanned layer during wafer inspection. Various details are set forth herein to provide a thorough understanding of the present invention to those skilled in the art, although many explicit details of materials, equipment and methodology are not set forth herein in detail so as not to unnecessarily obscure the present invention. Only the preferred embodiment of the present invention and but a few examples of its versatility are shown and described in the present disclosure and it is to be understood that the present invention is capable of use in other combinations and environments and contemplates modifications within the scope of the inventive concept expressed herein.

What is claimed is:

1. A variable illumination angle inspection system, comprising:
   a light source providing a light beam;
   a scanner imparting scanning deflection to the light beam to provide a scanning beam approaching a spot on a substrate surface at a first angle; and
   a deflection element selectively insertable into an optical path of the scanning beam and deflecting the scanning beam so as to cause the scanning beam to approach one of said spot and substantially said spot on said substrate surface at a second angle.

2. A variable illumination angle inspection system according to claim 1, wherein the first angle is normal to said surface of said substrate.

3. A variable illumination angle inspection system according to claim 2, wherein the second angle is oblique to said surface of said substrate.

4. A variable illumination angle inspection system according to claim 3, wherein the scanner comprises one of a scanning mirror, a rotating mirror, a polygonal mirror, and an acousto-optic deflector.

5. A variable illumination angle inspection system according to claim 4, wherein the deflection element comprises a mirror connected to an actuator arm.

6. A variable illumination angle inspection system according to claim 4, wherein the deflection element comprises a plurality of movable mirrors.

7. A variable illumination angle inspection system according to claim 6, wherein the movable mirrors are disposed to direct the scanning beam at the second angle to a focal position substantially corresponding to a focal position of the scanning beam approaching said surface of said substrate at the first angle.

8. A variable illumination angle inspection system according to claim 4,
   wherein the deflection element comprises a glass optical element including a first mirrored surface on a first side and a second mirror surface on a second side,
   wherein the scanning beam enters a third side and is reflected from the first mirrored surface and second mirrored surface obliquely toward said surface of said substrate at the second angle.

9. A variable illumination angle inspection system according to claim 8,
wherein a focal position of an oblique beam approaching said surface of said substrate from the second angle when the deflection element is in the optical path coincides with a focal position of a normal beam approaching said surface of said substrate from the first angle when the deflection element is not in the optical path.

10. A variable illumination angle inspection system according to claim 8,
wherein the first mirrored surface is a partially mirrored surface transmitting a portion of incident light and reflecting a portion of incident light, and
wherein a second glass optical element is disposed adjacent the first mirrored surface to focus light transmitted through the first mirrored surface onto the same coordinate of said surface of said substrate illuminated by the scanning beam reflected by the second mirrored surface toward said surface of said substrate at the second angle.

11. A variable illumination angle inspection system according to claim 10,
wherein a focal position of an oblique beam approaching said surface of said substrate from the second angle when the deflection element is in the optical path coincides with a focal position of a normal beam approaching said surface of said substrate from the first angle when the deflection element is not in the optical path.

12. A variable illumination angle inspection system according to claim 4,
wherein the deflection element comprises a first optical element, a second optical element, and a third optical element,
wherein one side the second optical element is adjacent the first optical element and another side of the second optical element is adjacent the third optical element,
wherein light incident to the deflection element includes both s- and p-polarizations in proportions selectable by use of at least one of a quarter-wave plate and a half-wave plate;
wherein a s-polarizing beamsplitting element is provided between the first optical element and the second optical element,
wherein a p-polarizing beamsplitting element is provided between the second optical element and the third optical element, and
wherein the scanning beam incident on the second optical element is output obliquely toward the substrate as s-polarized light and p-polarized light from the first optical element and the second optical element, respectively, and
wherein the foci of the two oblique output beams coincide on said surface of said substrate.

13. A variable illumination angle inspection system according to claim 12,
wherein a focal position of an oblique beam approaching said surface of said substrate from the second angle when the deflection element is in the optical path coincides with a focal position of a normal beam approaching said surface of said substrate from the first angle when the deflection element is not in the optical path.

14. A variable illumination angle inspection system for inspecting a substrate, comprising:
a light source providing a light beam;
a scanning element adapted to output the light beam along a first optical path to a spot on surface of said substrate, the first optical path including a portion incident to said spot on said surface of said substrate and forming a first angle relative to said surface of said substrate; and
a deflection element selectively introduced into the first optical path to output the light beam along a second optical path to one of said spot and substantially said spot on said surface of said substrate, the second optical path including a portion incident to said one of said spot and substantially said spot on said surface of said substrate and forming a second angle relative to said surface of said substrate,
wherein the first angle is different from the second angle.

15. A variable illumination angle inspection system for inspecting a substrate according to claim 14, wherein the first angle is oblique to said surface of said substrate and the second angle is substantially perpendicular to said surface of said substrate.

16. A variable illumination angle inspection system for inspecting a substrate according to claim 14, wherein the second angle is oblique to the substrate and the first angle is substantially perpendicular to said surface of said substrate.

17. A variable illumination angle inspection system according to claim 16,
wherein the deflection element comprises a first optical element, a second optical element, and a third optical element,
wherein one side the second optical element is adjacent the first optical element and another side of the second optical element is adjacent the third optical element,
wherein a s-polarizing beamsplitting element is provided between the first optical element and the second optical element,
wherein a p-polarizing beamsplitting element is provided between the second optical element and the third optical element, and
wherein the scanning beam incident on the second optical element is output obliquely toward the substrate as s-polarized light and p-polarized light from the first optical element and the second optical element, respectively.

18. A variable illumination angle inspection system according to claim 17,
wherein a focal position of an oblique beam approaching said surface of said substrate from the second angle when the deflection element is in the first optical path coincides with a focal position of a normal beam approaching said surface of said substrate from the first angle when the deflection element is not in the first optical path.

19. A variable illumination angle inspection system for inspecting a substrate according to claim 14, wherein the deflection element is selectively inserted into the first optical path by an actuator.

20. A variable illumination angle inspection system according to claim 19,
wherein the deflection element comprises a glass optical element including a first mirrored surface on a first side and a second mirror surface on a second side,
wherein the scanning light beam enters a third side and is reflected from the first mirrored surface and second mirrored surface obliquely toward said surface of said substrate at the second angle.

21. A variable illumination angle inspection system according to claim 20, wherein a focal position of an oblique beam approaching said surface of said substrate from the second angle when the deflection element is in the fist optical path coincides with a focal position of a normal beam approaching said surface of said substrate from the first angle when the deflection element is not in the first optical path.

22. A variable illumination angle inspection system according to claim 20, wherein the first mirrored surface is a partially mirrored surface transmitting a portion of incident light and reflecting a portion of incident light, wherein a second glass optical element is movably disposed adjacent the first mirrored surface to focus light transmitted through the partially mirrored surface onto the same coordinate of said surface of said substrate illuminated by the scanning beam reflected by the second mirrored surface toward said surface of said substrate at the second angle.

23. A variable illumination angle inspection system according to claim 22, wherein a focal position of an oblique beam approaching said surface of said substrate from the second angle when the deflection element is in the first optical path coincides with a focal position of a normal beam approaching said surface of said substrate from the first angle when the deflection element is not in the first optical path.

24. A variable illumination angle inspection system according to claim 14, wherein the scanning element comprises one of a scanning mirror, a rotating mirror, a polygonal mirror and an acousto-optic deflector.

* * * * *